United States Patent
Kiraly

(10) Patent No.: US 10,722,200 B2
(45) Date of Patent: Jul. 28, 2020

(54) APPARATUS AND METHODS FOR A PROJECTION DISPLAY DEVICE ON X-RAY IMAGING DEVICES

(71) Applicant: Siemens Healthcare GmbH, Erlangen (DE)

(72) Inventor: Atilla Peter Kiraly, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 275 days.

(21) Appl. No.: 15/515,213

(22) PCT Filed: Jun. 4, 2015

(86) PCT No.: PCT/US2015/034098
§ 371 (c)(1),
(2) Date: Mar. 29, 2017

(87) PCT Pub. No.: WO2016/195684
PCT Pub. Date: Dec. 8, 2016

(65) Prior Publication Data
US 2017/0209110 A1 Jul. 27, 2017

(51) Int. Cl.
*A61B 6/00* (2006.01)
*A61B 6/04* (2006.01)
(Continued)

(52) U.S. Cl.
CPC .............. *A61B 6/467* (2013.01); *A61B 6/04* (2013.01); *A61B 6/0407* (2013.01);
(Continued)

(58) Field of Classification Search
CPC .. A61B 6/08; A61B 6/10; A61B 6/102; A61B 6/44; A61B 6/4429; A61B 6/4435;
(Continued)

(56) References Cited

U.S. PATENT DOCUMENTS 4,246,486 A * 1/1981 Madsen ................. A61B 6/587
378/206
4,293,771 A * 10/1981 Lescrenier ............... A61B 6/08
356/138
(Continued)

FOREIGN PATENT DOCUMENTS

DE 1020027526 1/2012
DE 102012201798 8/2013
(Continued)

OTHER PUBLICATIONS

International Search Report dated Jan. 29, 2016 in corresponding International Application No. PCT/US2015/034098.

*Primary Examiner* — Allen C. Ho

(57) ABSTRACT

Apparatuses and methods are provided for projecting a display of information for an x-ray device. The display of information is projected on the patient, on the table 205 area or on a combination thereof. A compact projector 207 is provided to project the display of information on a previously unused region of the patient and table 207, and provides a source of diagnostic and safety information without further crowding the room. The projected display of information may be a system state, a patient state, a surgical tool position or another relevant image. A compact sensor or range scanner 209 may be employed to capture three-dimensional distance information in the x-ray system. The three-dimensional distance information may be used to reduce distortion in the projected image, selectively darken regions of the projected image, automatically configure the x-ray system, capture inputs from the operator and improve safety in the x-ray system.

15 Claims, 4 Drawing Sheets

(51) Int. Cl.
*A61B 6/08* (2006.01)
*A61B 6/10* (2006.01)
*A61B 90/35* (2016.01)
*G03B 29/00* (2006.01)
*A61B 6/06* (2006.01)
*A61B 90/00* (2016.01)
*A61B 90/30* (2016.01)

(52) U.S. Cl.
CPC ............ *A61B 6/0492* (2013.01); *A61B 6/08* (2013.01); *A61B 6/10* (2013.01); *A61B 6/102* (2013.01); *A61B 6/42* (2013.01); *A61B 6/4208* (2013.01); *A61B 6/4258* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/46* (2013.01); *A61B 6/461* (2013.01); *A61B 6/462* (2013.01); *A61B 6/463* (2013.01); *A61B 6/464* (2013.01); *A61B 6/465* (2013.01); *A61B 6/466* (2013.01); *A61B 6/469* (2013.01); *A61B 90/35* (2016.02); *G03B 29/00* (2013.01); *A61B 6/06* (2013.01); *A61B 90/30* (2016.02); *A61B 2090/366* (2016.02)

(58) Field of Classification Search
CPC ......... A61B 6/4441; A61B 6/46; A61B 6/461; A61B 6/462; A61B 6/463; A61B 6/464; A61B 6/465; A61B 6/466; A61B 6/467; A61B 6/04; A61B 6/0407; A61B 6/0492; A61B 6/42; A61B 6/4208; A61B 6/4258; A61B 6/4447; A61B 6/469
USPC ..... 378/62, 91, 95, 98, 98.2, 98.3, 162–166, 378/196–198, 204–207
See application file for complete search history.

(56) References Cited

U.S. PATENT DOCUMENTS

| | | | | |
|---|---|---|---|---|
| 4,356,400 A * | 10/1982 | Polizzi | ............... | A61B 6/587 250/252.1 |
| 4,426,726 A * | 1/1984 | Cheetham | ............ | A61B 90/13 378/206 |
| 4,570,268 A * | 2/1986 | Freeman | ............ | A41D 13/1236 2/114 |
| 4,622,699 A * | 11/1986 | Spriggs | ............. | A41D 13/1236 2/114 |
| 4,836,671 A * | 6/1989 | Bautista | ............. | A61B 6/08 250/491.1 |
| 4,969,215 A * | 11/1990 | Burkett | ............. | A41D 13/1236 2/114 |
| 5,316,014 A * | 5/1994 | Livingston | ......... | A61B 17/3403 378/206 |
| 5,517,546 A * | 5/1996 | Schmidt | ............. | A61B 6/08 378/205 |
| 5,553,115 A * | 9/1996 | Odaka | ............... | A61B 6/08 378/170 |
| 5,572,568 A * | 11/1996 | Kanemitsu | ............. | A61B 6/08 378/190 |
| 5,598,269 A * | 1/1997 | Kitaevich | ............. | A61B 6/08 356/399 |
| 5,657,368 A * | 8/1997 | Röckseisen | ............. | A61B 6/08 378/205 |
| 6,036,362 A * | 3/2000 | Schmitt | ............... | A61B 6/08 378/150 |
| 6,041,249 A * | 3/2000 | Regn | ................... | A61B 6/08 378/20 |
| 6,044,291 A * | 3/2000 | Röckseisen | ............. | A61B 6/08 378/206 |
| 6,279,579 B1 * | 8/2001 | Riaziat | ............... | A61N 5/1049 128/897 |
| 6,447,164 B1 * | 9/2002 | Polkus | ................. | A61B 6/08 378/205 |
| 6,496,558 B2 * | 12/2002 | Graumann | ........... | A61B 6/0478 378/197 |
| 6,502,984 B2 * | 1/2003 | Ogura | ................ | A61B 6/06 378/206 |
| 6,690,965 B1 * | 2/2004 | Riaziat | ................. | A61B 6/463 378/62 |
| 6,842,175 B1 * | 1/2005 | Schmalstieg | ........... | G06F 3/011 345/427 |
| 6,917,666 B2 * | 7/2005 | Wollenweber | ........... | A61B 6/04 378/20 |
| 6,937,696 B1 * | 8/2005 | Mostafavi | ............ | A61B 5/113 378/65 |
| 6,942,385 B2 * | 9/2005 | Fadler | ................ | A61B 6/08 378/205 |
| 7,014,362 B2 * | 3/2006 | Beimier | ............... | A61B 6/08 378/162 |
| 7,040,807 B2 * | 5/2006 | Scheuering | .............. | A61B 6/08 356/399 |
| 7,054,412 B2 * | 5/2006 | Scheuering | ........... | A61B 6/544 378/108 |
| 7,147,371 B2 * | 12/2006 | Hecker | .................. | A61B 6/08 378/206 |
| 7,177,386 B2 * | 2/2007 | Mostafavi | ............ | A61B 5/1135 378/4 |
| 7,273,280 B2 * | 9/2007 | Smoot | ................... | G03B 15/10 353/30 |
| 7,343,026 B2 * | 3/2008 | Niwa | .................... | A61B 6/467 382/103 |
| 7,372,935 B2 * | 5/2008 | Bernhardt | ............. | A61B 5/107 378/4 |
| 7,428,296 B2 * | 9/2008 | Bernhardt | ............. | A61B 6/102 378/117 |
| 7,490,986 B2 * | 2/2009 | Takekoshi | ............ | A61B 6/4441 378/205 |
| 7,496,174 B2 * | 2/2009 | Gertner | ................ | A61N 5/1017 378/65 |
| 7,559,693 B2 * | 7/2009 | Sonani | ..................... | A61B 6/08 378/206 |
| 7,581,884 B1 * | 9/2009 | Barnes | ..................... | A61B 6/06 378/164 |
| 7,620,147 B2 * | 11/2009 | Gertner | ................... | A61N 5/10 378/145 |
| 7,632,015 B2 * | 12/2009 | Stayman | ................ | A61B 6/032 378/163 |
| 7,677,801 B2 * | 3/2010 | Pakzaban | ............. | A61B 5/103 378/162 |
| 7,697,147 B2 * | 4/2010 | Kindlein | .................. | A61B 6/08 356/601 |
| 7,736,055 B2 * | 6/2010 | Hörnig | ..................... | A61B 6/08 378/206 |
| 7,737,427 B2 * | 6/2010 | Kito | ..................... | A61B 6/4233 250/370.08 |
| 7,742,569 B2 * | 6/2010 | Graumann | ............. | A61B 6/00 378/206 |
| 7,794,144 B2 * | 9/2010 | Windt | ..................... | A61B 6/08 378/206 |
| 7,802,919 B2 * | 9/2010 | Hessert | .................. | B23Q 17/24 378/206 |
| 7,806,591 B2 * | 10/2010 | Wang | ..................... | A61B 6/00 378/196 |
| 7,878,710 B2 * | 2/2011 | Kashiwagi | ............. | A61B 6/502 378/206 |
| 7,924,980 B2 * | 4/2011 | Ohta | ....................... | A61B 6/00 250/370.09 |
| 7,934,869 B2 * | 5/2011 | Ivanov | ................ | A61N 5/1049 378/20 |
| 8,155,269 B2 * | 4/2012 | Kobayashi | ............ | A61B 6/08 378/164 |
| 8,165,660 B2 * | 4/2012 | Pfister | ................... | A61B 6/12 378/205 |
| 8,315,356 B2 * | 11/2012 | Core | ................... | A61N 5/1049 378/205 |
| 8,317,394 B2 * | 11/2012 | Klemm | ................... | A61B 6/08 378/108 |

(56) References Cited

U.S. PATENT DOCUMENTS

| | | | | |
|---|---|---|---|---|
| 8,371,751 B2* | 2/2013 | Vazquez | A61B 5/1128 | 378/206 |
| 8,390,821 B2* | 3/2013 | Shpunt | G01B 11/25 | 356/512 |
| 8,434,942 B2* | 5/2013 | Lenchig, Jr. | A61B 6/08 | 378/204 |
| 8,526,573 B2* | 9/2013 | Ferro, Jr. | A61B 6/4429 | 378/98 |
| 8,553,839 B2* | 10/2013 | Hendriks | A61B 6/4441 | 378/63 |
| 8,570,372 B2* | 10/2013 | Russell | G06F 3/013 | 348/136 |
| 8,670,521 B2* | 3/2014 | Bothorel | A61B 6/14 | 378/205 |
| 8,717,417 B2* | 5/2014 | Sali | H04N 13/254 | 348/46 |
| 8,737,705 B2* | 5/2014 | Pearson, Jr. | G06K 9/00221 | 382/128 |
| 8,798,720 B2* | 8/2014 | Bill | A61B 6/06 | 378/156 |
| 8,821,015 B2* | 9/2014 | Stagnitto | A61B 6/4291 | 378/205 |
| 8,824,630 B2* | 9/2014 | Maurer, Jr. | G06F 19/3481 | 378/20 |
| 8,824,634 B2* | 9/2014 | Lalena | A61B 6/08 | 378/108 |
| 8,827,554 B2* | 9/2014 | Lalena | A61B 6/46 | 378/206 |
| 8,873,708 B2* | 10/2014 | Sugiyama | A61B 6/06 | 378/151 |
| 8,873,709 B2* | 10/2014 | Kimura | A61B 6/4429 | 378/165 |
| 8,873,712 B2* | 10/2014 | Wang | A61B 6/08 | 378/97 |
| 8,971,486 B2* | 3/2015 | Scholling | G01N 23/02 | 378/57 |
| 9,008,269 B2* | 4/2015 | Wang | A61B 6/52 | 378/146 |
| 9,028,144 B2* | 5/2015 | Choi | A61B 6/032 | 378/205 |
| 9,039,283 B2* | 5/2015 | Graumann | A61B 6/08 | 378/205 |
| 9,053,574 B2* | 6/2015 | Ernvik | G06T 15/08 | |
| 9,060,740 B2* | 6/2015 | Lindenberg | G01B 11/25 | |
| 9,204,116 B2* | 12/2015 | Schmidt | H04N 9/3129 | |
| 9,226,708 B2* | 1/2016 | Kim | A61B 5/4848 | |
| 9,235,973 B2* | 1/2016 | Popescu | G08B 21/02 | |
| 9,254,109 B2* | 2/2016 | Becker | A61B 6/032 | |
| 9,332,951 B2* | 5/2016 | Inglese | A61B 6/08 | |
| 9,389,190 B2* | 7/2016 | Tsuyuki | G01N 23/046 | |
| 9,433,395 B2* | 9/2016 | Kang | A61B 6/544 | |
| 9,439,619 B1* | 9/2016 | Nance | A61B 6/587 | |
| 9,480,443 B2* | 11/2016 | Feuerlein | A61B 6/032 | |
| 9,517,036 B2* | 12/2016 | Mostafavi | A61B 6/035 | |
| 9,589,336 B2* | 3/2017 | Flohr | A61B 6/032 | |
| 9,636,079 B2* | 5/2017 | Bredno | A61B 6/582 | |
| 9,642,584 B2* | 5/2017 | Niebler | A61B 6/4441 | |
| 9,649,080 B2* | 5/2017 | Kwak | A61B 6/4429 | |
| 9,736,402 B2* | 8/2017 | De Bruijn | G01J 5/0896 | |
| 9,737,280 B2* | 8/2017 | Manke | A61B 6/08 | |
| 9,763,599 B2* | 9/2017 | Graumann | A61B 5/0073 | |
| 9,782,136 B2* | 10/2017 | Zhou | A61B 6/547 | |
| 9,811,902 B2* | 11/2017 | Flohr | G06K 9/4604 | |
| 9,820,705 B2* | 11/2017 | Kim | A61B 6/08 | |
| 9,833,209 B2* | 12/2017 | Belei | A61B 6/4441 | |
| 9,861,327 B2* | 1/2018 | Yasuda | A61B 6/06 | |
| 9,904,998 B2* | 2/2018 | Jockel | A61B 6/08 | |
| 9,907,518 B2* | 3/2018 | Gooßen | A61B 6/0492 | |
| 9,918,692 B2* | 3/2018 | Kawamura | A61B 6/461 | |
| 9,924,872 B2* | 3/2018 | Harada | A61B 6/08 | |
| 9,931,088 B2* | 4/2018 | Grasruck | A61B 6/08 | |
| 9,943,271 B2* | 4/2018 | Dirauf | A61B 6/545 | |
| 9,949,699 B2* | 4/2018 | Visser | G06T 11/003 | |
| 9,955,927 B2* | 5/2018 | Hendriks | A61B 6/025 | |
| 9,993,216 B2* | 6/2018 | Flohr | A61B 6/5205 | |
| 10,098,607 B2* | 10/2018 | Grasruck | A61B 6/582 | |
| 10,143,428 B2* | 12/2018 | Eun | A61B 6/04 | |
| 10,143,532 B2* | 12/2018 | Samsonov | A61B 90/39 | |
| 10,181,074 B2* | 1/2019 | Braun | A61B 6/0457 | |
| 10,220,181 B2* | 3/2019 | Giap | A61N 5/1068 | |
| 10,285,656 B2* | 5/2019 | Wang | A61B 6/4405 | |
| 10,285,660 B2* | 5/2019 | Zaiki | A61B 6/54 | |
| 10,376,217 B2* | 8/2019 | Schmidt | A61B 5/0555 | |
| 10,403,402 B2* | 9/2019 | Ziraknejad | A61B 90/37 | |
| 10,448,003 B2* | 10/2019 | Grafenberg | A61B 6/5247 | |
| 2005/0058256 A1 | 3/2005 | Beimler et al. | | |
| 2006/0079763 A1 | 4/2006 | Jeung et al. | | |
| 2006/0235849 A1 | 10/2006 | Schmidt et al. | | |
| 2006/0274888 A1 | 12/2006 | Bernhardt et al. | | |
| 2008/0094589 A1 | 4/2008 | Panitz | | |
| 2008/0198968 A1 | 8/2008 | Takekoshi et al. | | |
| 2009/0141958 A1 | 6/2009 | Graumann et al. | | |
| 2013/0342350 A1 | 12/2013 | Popescu et al. | | |
| 2014/0241511 A1 | 8/2014 | Hausotte et al. | | |

FOREIGN PATENT DOCUMENTS

| | | |
|---|---|---|
| DE | 102013215516 | 2/2015 |
| JP | 2011120785 | 6/2013 |
| JP | 2014097131 | 5/2014 |
| WO | WO2011063266 | 5/2011 |
| WO | WO2015018566 | 2/2015 |

* cited by examiner

APPARATUS AND METHODS FOR A PROJECTION DISPLAY DEVICE ON X-RAY IMAGING DEVICES

BACKGROUND

Interventional radiology suites and operating rooms have limited space for surgical tools and equipment, but contain the x-ray device and a multitude of displays, equipment and additional components. During surgery and other procedures, support staff and assisting physicians are also present in addition to the operator, such as a surgeon or radiologist. Procedures usually take place in a darkened room with the operator constantly having to look up at multiple displays for guidance. The multiple displays further crowd the operating room. Additionally, operator input options are limited by the available space in the room and introducing new devices or prototypes frequently require additional equipment and displays in the already crowded room. Introducing additional equipment also often involves complex wiring and interfaces between devices to utilize existing displays and operator input devices. There is a need to make better use of existing space without adding bulky equipment. Furthermore, operator interfaces requiring direct physical contact can be cumbersome or difficult to use during procedures. There is a need for operator interfaces without direct physical contact to allow for easier sterilization and for more intuitive operator interfaces.

SUMMARY

The present embodiments relate to projection display devices for x-ray imaging devices. By way of introduction, the present embodiments described below include apparatuses and methods for a projected display of information and/or other images during use, setup, calibration and/or marketing of an x-ray device, such as a C-arm fluoroscopy device. A projected display of information and/or other images improves safety may allow for fast and intuitive operator interfaces and provides for marketing opportunities. The information and/or other images are projected on the patient, on the x-ray table or on a combination thereof. The projected display of information and/or other images are used as a direct visible source of information to the operator. A compact projector projects display of information and/or other images on the previously unused region of the patient and/or table, providing a source of diagnostic and/or safety information without further crowding the room. The display of information and/or other images may be a system state, a patient state, a surgical tool position or another relevant image. A compact sensor, range scanner or range imager may be employed to capture two-dimensional or three-dimensional distance information in the x-ray system. The distance information is used to reduce distortion in the projected image, selectively darken regions of the projected image, automatically configure the x-ray system, capture inputs from the operator, and/or improve safety in the x-ray system. The range imaging device is associated with the projector to receive input from the projected scene that is used for machine input and for safety through collision avoidance.

In a first aspect, an x-ray system is provided including an x-ray emitter, an x-ray detector and a table configured for receiving an object to be irradiated. The x-ray system includes a projector configured to project a display of information on the table, on the object to be irradiated, or on the table and the object.

In a second aspect, a C-arm x-ray system is provided including a C-arm having a first end and second end. An x-ray source is mounted to the first end of the C-arm and an x-ray detector is mounted to the second end. The x-ray system includes a table configured for receiving a patient to be irradiated and a projector configured to project a display of information on the table, on the patient, or on the table and the patient.

In a third aspect, a method for a projection display on an x-ray imaging device is provided. The method includes orienting an x-ray source and x-ray detector relative to the table and projecting a display of information on the table, on an object to be irradiated on the table, or on the table and the object, using a projector. The projected display of information includes an x-ray device state, a patient state, a surgical tool position, an image captured by the x-ray imaging device or a marketing image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EXEMPLARY EMBODIMENTS

The present embodiments provide a projection display for an x-ray system, such as on a C-Arm of fluoroscopy device or other x-ray system. The projection display projects a display of information and/or other images on an x-ray table and/or a patient, providing the operator with a source of information for safety, guidance, and/or calibration. The projection display also provides improved ergonomics. One or more projectors allow the x-ray system to provide information for multiple applications to be displayed concurrently. The one or more projectors are incorporated with x-ray imaging devices to offer additional data and device status efficiently and intuitively. A range scanner, sensor or range imager may also be incorporated allowing for additional input and scanning possibilities. Using the projected display of information takes up no additional space in the room and incorporating a range scanner results in an intuitive, touch-free operator interface. The projector and range scanner further allow for a focus-free projection system with limited distortion across display surfaces.

The projection display device on an x-ray system may improve diagnostic and calibration efficiency by providing the operator with direct feedback via the projected display of information. The projection display device may provide the operator with direct visual feedback during a procedure, such as by providing an electrocardiogram (ECG) and other relevant patent information, by displaying an instrument location, and/or by projecting other relevant information and/or images. The projection display of information may enhance the safe use of the x-ray system, such as by indicating the status of the system (i.e., on or off; active or inactive) and the optional range scanner may automatically calibrate the position, angular orientation, exposure time and radiation level for the patient. The projection display device may provide improved x-ray system status indication and may facilitate enhanced debugging of the x-ray system. The projection display device may also differentiate the x-ray system, or a feature of the x-ray system, from the market by setting the projection display device in a marketing mode. By projecting advertising, funds may be raised or the system may be better distinguished from competitors at trade shows. Additionally, during system downtimes, information on the next maintenance dates or new company products can be displayed.

Figure 1:
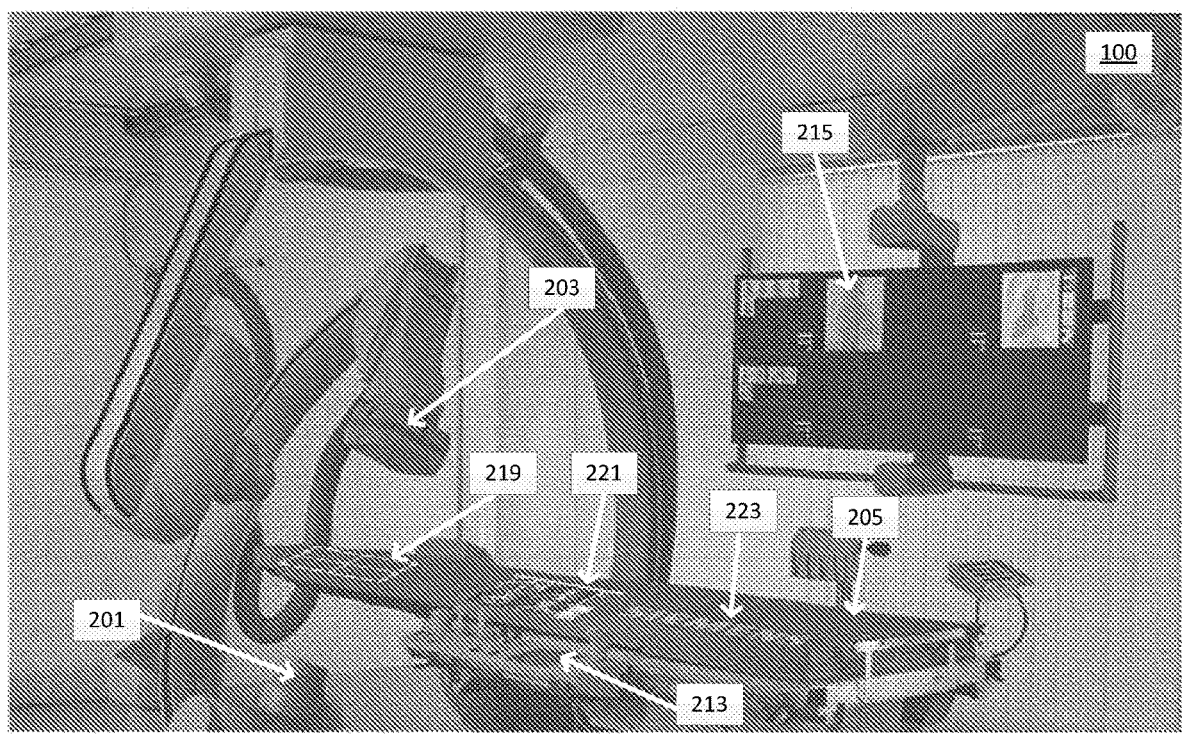
FIG. 1 illustrates an example of a display of information from a projection display device on an x-ray imaging device table.

FIG. 1 illustrates an example of a display of information from a projection display device on an x-ray imaging device table. FIG. 1 depicts a rendering of an embodiment of an x-ray system 100 with multiple projectors. In this example, the x-ray system 100 is a C-arm collimator. Other medical imaging systems are contemplated, such as a magnetic resonance (MR) or computerized tomography (CT) scanner. The x-ray system 100 includes an x-ray emitter or source 201, an x-ray detector 203 and a table 205. The x-ray system 100 includes an operator interface 213 for controlling the x-ray system 100, including, for example, joysticks and other input devices. The x-ray system 100 also includes a display panel 215. The display panel 215 is typically mounted above the table 205. One or more projectors (not depicted in FIG. 1) are mounted to the x-ray emitter or source 201, to the x-ray detector 203, to another component of the x-ray system 100, in a ceiling, on a wall, or anywhere with a direct line of sight to the table 205 (e.g., to the ceiling above the x-ray system 100). Additional, different, or fewer components may be provided.

In the rendering depicted in FIG. 1, one or more projectors (not depicted in FIG. 1) project a display of information and/or other images on the table 205, providing the operator with information about the system state, the patient state, one or more surgical tool positions and/or other information. For example, a system state 219, such as collimator settings, is projected directly onto the region of the table 205 to be scanned (i.e., irradiated). In this example, no patients or other objects are place on the table 205. For example, the system state 219 can be used without a patient or other object during maintenance, calibration, setup or the like. In another example, collimator settings are projected directly onto the patient or other object to be scanned. Further, as depicted in FIG. 1, a patient state 221 is projected directly onto the table 205. For example, a patient state 221 includes the patient's electrocardiogram (ECG), blood pressure and other vital signs. Additionally or alternatively, a patient state 221 includes a fluoroscopy or other image, a series of captured images (e.g., previously captured (preop) and replayed images, or images captured in real-time), another relevant image or a combination thereof (e.g., an image superimposed over another image). Finally, as depicted in FIG. 1, marketing information 223 is projected directly on the table 205. For, example, the marketing information 223 is a company logo that is included for marketing purposes, such as for display during a startup routine or at a trade show. Additional, different, or fewer types of information may be projected.

The projected display of information and/or other images, including the system state 219, the patient state 221, and the marketing information 223 are provided in addition to, or in replacement of, the display panel 215. Frequently, the display panel 215 is an overhead monitor, a built-in display and/or support computers used to communicate information to the operator. The projected display of information and/or other images allow information to be communicated to the operator without the operator diverting attention away from the patient and/or the table, or the operator having to constantly look up or move to view the display panel 215. Use of two or more projectors can further alleviate the need for the operator to divert attention to the display panel 215, such as during calibration by displaying various test images on table 205. During a procedure, the projected display of information and/or other images increase efficiency and ergonomics associated with the procedure by alleviating the need to divert the operator's attention from the patient to view display panel 215. For example, collimator settings and an X-ray status can be projected as lines across the patient or object being irradiated, and adjustments to the collimator are projected directly on the table without the operator having to look to the overhead display panel 215. Further, an optional range scanner or other sensor (not depicted in FIG. 1) can be included in x-ray system 100. The range data may be used to calibrate and service the x-ray system 100, to reduce distortion in the display of information and/or other images, and to improve safe use of the x-ray system 100.

Figure 2:
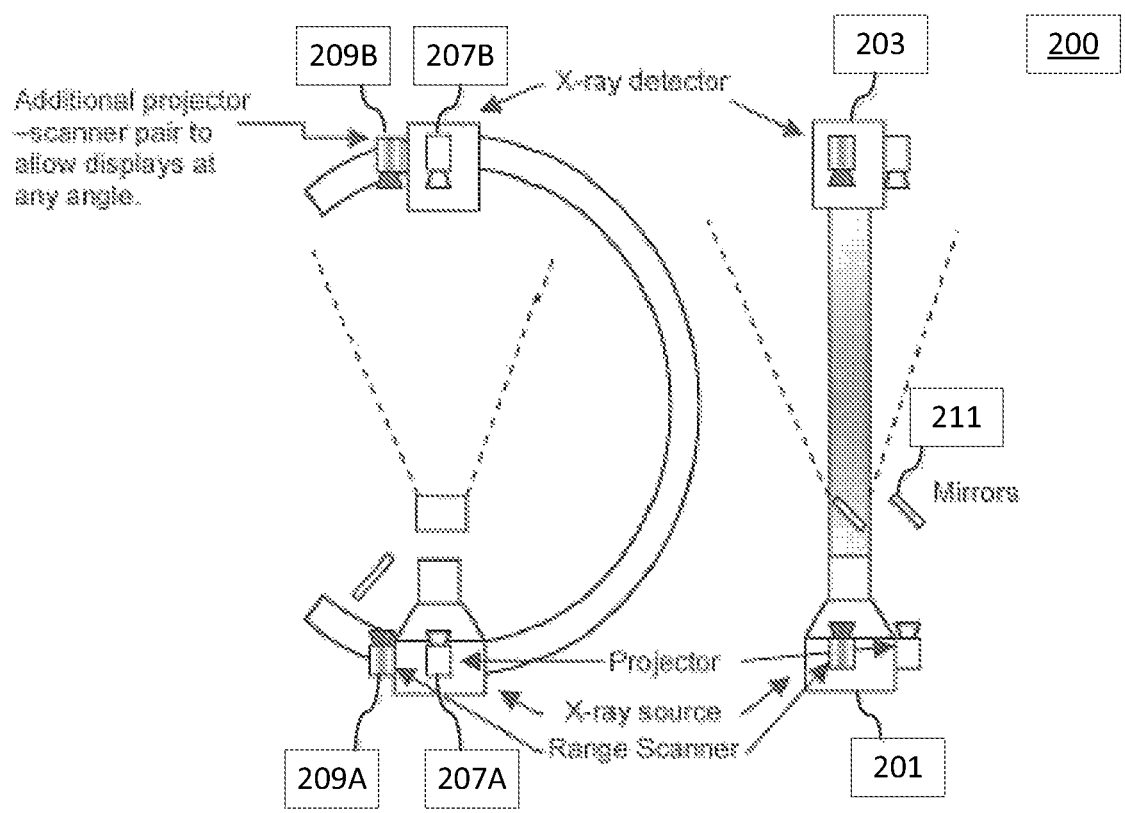
FIG. 2 illustrates an embodiment of a system for a projection display device mounted to an x-ray imaging device C-arm.

FIG. 2 illustrates an embodiment of a system for a projection display device mounted to an x-ray imaging device C-arm. The x-ray system 200 includes an x-ray emitter or source 201, an x-ray detector 203, projectors 207A and 207B, range scanners or sensors 209A and 209B, and radio-transparent mirrors 211. Additional, different, or fewer components may be provided. For example, fewer or additional projectors and range scanners may be provided, such as on multiple C-arms. Further, a radio-transparent surface may be placed over the object to be irradiated.

Figure 3:
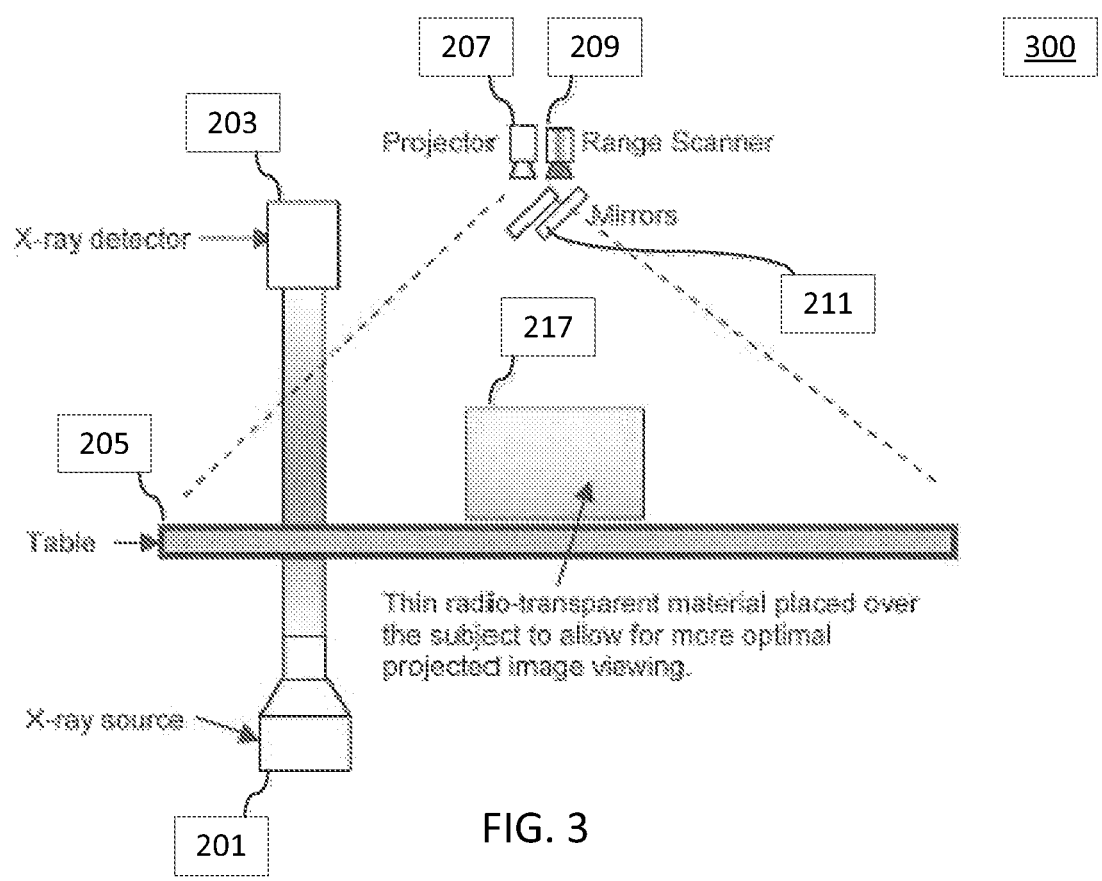
FIG. 3 illustrates an embodiment of a system for a projection display device mounted above an x-ray imaging device table

FIG. 3 illustrates another embodiment of a system for a projection display device mounted above an x-ray imaging device table. The x-ray system 300 includes an x-ray emitter or source 201, an x-ray detector 203, a projector 207, a range scanner or sensor 209, radio-transparent mirrors 211 and a radio-transparent material 217. Additional, different, or fewer components may be provided. In this embodiment, the projector 207 and the range scanner or sensor 209 are mounted in a fixed location relative to the table 205, such as to the ceiling above the table 205. Alternatively, the projector 207 and the range scanner or sensor 209 are mounted in a semi-fixed location relative to the table 205, such as on a sliding mechanism mounted to the ceiling above the table 205. In another embodiment, the projector 207 is mounted to the ceiling above table 205 and the projectors 207A and 207B are mounted to the C-Arm. In this embodiment, a fixed (ceiling mount) and moving (C-arm mount) source of projections are provided. Other combinations of one or more projectors mounted in the x-ray system 300 are contemplated, such as combinations of projectors mounted to an x-ray emitter or source 201, an x-ray detector 203 and/or mounted in a fixed location or semi-fixed location.

The present embodiments enhance existing x-ray systems 100, 200 and 300. For example, the projector(s) 207 and 207A, and the optional range scanner(s) or sensor(s) 209 and 209A, are mounted to the X-ray emitter or source 201.

Radio-transparent mirrors 211 direct the projectors 207 and 207A output directly on the irradiated or other region of the table 205 and/or on the objected being irradiated. The radio-transparent mirrors 211 direct the projectors 207 and 207A to the match the field of view of the x-ray emitter or source 201 without blocking x-rays from the X-ray emitter or source 201. The radio-transparent material 217 provides a smooth surface to capture the projected image without interfering with the x-ray image acquisition. Alternatively, the output of the projector 207 and 207A is projected on another surface in the room. A range-scanner or sensor 209 and 209A is optionally used to capture two-dimensional or three-dimensional range data for surface, the table 205 and/or the objected being irradiated. By detecting the two-dimensional data or three-dimensional shape of the surface on which the projected image is displayed, the projected output may be adjusted to reduce distortions on uneven surfaces. Further, the range-scanner or sensor 209 and 209A serves as an input to the x-ray system in order to track the C-arms and other objects in the range scanner or sensor's field of view. In another example, a projector 207B and a range scanner or sensor 209B are also be placed on the x-ray detector 203 allowing for projected images regardless of the orientation of the C-arm.

The x-ray systems 100, 200 and 300 include an x-ray emitter or source of 201 and an x-ray detector 203. In an example, the x-ray system is a monoplane C-arm system having two ends. In this example, the x-ray emitter or source 201 is mounted to one end of the C-arm and the x-ray detector 203 is mounted to the other end of the C-arm. In another example, the x-ray system is a biplane C-arm system, have two C-arms, with each C-arm having an x-ray emitter or source 201 and an x-ray detector 203. The x-ray systems 100, 200 and 300 are configured to acquire x-ray images of a patient or other object by irradiating the examination object with x-rays directed at the object from one or more locations in space using the x-ray emitter or source 201 and the x-ray detector 203 mounted to one or more C-arms. The x-ray systems 100, 200 and 300 also include a table 205 or other surface that receives the other object to be irradiated.

The x-ray systems 100, 200 and 300 include one or more projectors 207, 207A and 207B. The projectors 207, 207A and 207B are configured to project a display of information or other images onto the table 205, on the object, on the table 205 and the object, or on another surface. The projectors 207, 207A and 207B are provided using any now existing or future projector technology, such as standard bulb projector or a laser projector. Preferably, the projectors 207, 207A and 207B are provided in a compact design. For example, laser projectors are provided. Laser projectors are compact and more energy efficient than standard bulb projectors and allow for a wide range of focused projections in full color. The projectors 207, 207A, and/or 207B project two-dimensional images. The projections have three or more levels of brightness. While a single color may be used, two or more colors are provided in other embodiments. For example, the projector has 128 more or levels of brightness using 32 or more different colors, allowing for a two-dimensional image communicating more information than a dot or grid.

The projected display of information or other images allow the operator to view the display of information or other relevant images without having to divert attention away from the table 205, such as to view an overhead display panel 215, a built-in display or a support computer used to communicate information to the operator. For example, the projected display of information or other relevant images communicate an x-ray system status; a device status; a patient state or other relevant patient information; a surgical tool position; safety information; and/or marketing information. Additional, different, or less information may be provided.

For example, the projected display of information or other images allow for x-ray system status and device states to be displayed on the table 205 without the operator or service technician having to constantly move back from the x-ray system to view the display panels 215. Two or more projectors are used during calibration displaying test images. The optional range scanner(s) or sensors 209, 209A and 209B are used to detect objects on the table 205 to better calibrate or service the x-ray system. In another example, the projected display of information or other images serve as a step-by-step guidebook for maintenance, calibration and operation. The large, movable projections permit the technician to observe instructions without confining the instructions to a small fixed display or in a set location. The projections also allow for faster and more intuitive maintenance and setup, and better ergonomics for the operator.

During a procedure, the projected display of information or other images increase efficiency and ergonomics. For example, an x-ray system setting, such as one or more collimator settings, and an x-ray status, such as projecting different colors when the collimator is on or off (e.g., active or inactive), is projected across the patient or object being irradiated. In this example, adjustments to the collimator are projected directly on the table 205 without the operator diverting attention to the overhead display panel 215. In another example, depending on the procedure being performed and the distance from the x-ray emitter or source 201 and x-ray detector 203 from the patient or object being irradiated, the projected display of information or other images are projected directly on the patient. In another example, the projected display of information or other images are projected on another region of the table 205. In this example, during an interventional radiology procedure, a catheter is inserted into the patient's leg and driven to the heart. A representation of the catheter may be projected onto the patient (e.g., in a different color). In another example, one or more real-time fluoroscopy images are projected, providing the operator with a direct contextual reference without diverting the operator's attention to an overhead display panel 215. In this example, a previously captured fluoroscopy image, or a sequence of a previously captured images, may also be projected. In a further example, a patient state 221 includes the patient's electrocardiogram (ECG), blood pressure and other vital signs are overlaying a fluoroscopy image, or are projected independently. In the event that the C-arm is too close to the patient's chest to allow for a clear view of the projected display of information, the projected display of information is provided near the imaging site, such as projecting collimator settings on table 205 next to the patient.

The projected display of information or other images may display safety information. For example, the projector 207, 207A, and 207B can emit a display of information or other images in different colors and different images based upon the status of the x-ray emitter or source 201. Traditionally, an x-ray light is provided at the entrance to a room signifying when the x-ray system is active. In this example, a red warning image is also projected notifying operators with a direct view of the projected display of information the status of the x-ray system, without having to rely on the x-ray light or other warning. Further, to prevent the C-arm from colliding with objects in close proximity to the x-ray system, the optional range scanner or sensor 209, 209A, and 209B is used to identify obstructions, allowing the x-ray system to limit the C-arm movement to avoid potential damage to the C-arm and other devices, and to prevent injury to the operator and the patient.

The projected display of information or other images provides marketing opportunities. For example, a company logo is projected, such as marketing information 223, during the x-ray system startup routine. The company logo is projected on the table 205 during system startup. In an example, a company or product logo is projected along with a countdown. Alternatively, the company or product logo is permanently projected, such as during a trade-show, a sale call or during other marketing events. Additional marketing images may also be projected. For example, because the projector 207, 207A, and 207B is not limited to projecting a single image, a full color video presents additional marketing opportunities allowing the projector 207, 207A, and 207B to be tailored to project additional content and marketing ideas. In an example, an x-ray system includes a "Demo Mode" or "Marketing Mode" that is enabled for trade shows, sale calls and other marketing events. In addition to the company logo, system features and system highlights can also be displayed in an animated fashion, allowing the x-ray system to stand out visually and distinguishing the x-ray system from competing systems. In the trade show example, x-ray system is often provided without the x-ray detector and emitter units for various reasons, such as to save shipping weight and other costs. In this example, the projector 207, 207A, and 207B and range scanner or sensor 209, 209A, and 209B may be included because one or more compact projectors and range scanners add only negligible weight and cost to the x-ray system.

The x-ray systems 100, 200 and 300 include one or more range scanners or sensors 209, 209A and 209B configured to capture 3D distance measurements for the x-ray systems 100, 200 and 300. A range scanner is a sensor, a range finder or other range detection device that captures two-dimensional (2D) or three-dimensional (3D) distance measurements. For example, a range scanner or sensor 209, 209A and 209B captures an image with distance measurements. In one implementation, the range scanner or sensor 209, 209A and 209B captures an image consisting of colored pixels and captures the distance of each pixel to the range scanner or sensor 209, 209A and 209B. In an implementation, the distance measurements are used by the x-ray system to map all surfaces in the range scanner's field of view. The range scanners or sensors 209, 209A and 209B are provided employing any now existing or future range detection technology. Preferably, the range scanners or sensors 209, 209A and 209B are provided in a compact design. For example, compact cameras and sensors for mobile phones (e.g., Capri 1.25 by PrimeSense) and full-size systems (e.g., Carmine 1.09 by PrimeSense) may be provided. Such systems are often provided with application program interfaces (API) for range image data processing and gesture recognition processing functionality. The range scanner or sensor 209, 209A, 209B may interact with the projector 207, 207A, 207B, such as the projecting a grid pattern used to determine range or surface shape.

The range scanners or sensors 209, 209A and 209B capture range data for the table 205, the objecting being irradiated, and/or the area surrounding the table 205. For example, the three-dimensional range data is used for the following applications: to adjust the projected image parameters and to limit distortion in the projected image; to calibrate the x-ray system and to automatically orient and configure the table 205 and scanner parameters to the object being irradiated; to prevent collisions with the x-ray system; and to receive operator inputs. Additional, different, or fewer applications may be provided.

The range data is used to adjust the projected display of information or other images by adjusting the projection parameters to limit distortion and to improve focus in the projected display of information or other images. For example, mounting a range scanner or sensor 209, 209A and 209B with the same or similar field of view as a projector 207, 207A and 207B enables the range scanner or sensor 209, 209A, and 209B to collect three-dimensional range data used to adjust the projector output by adjusting the shape and focus of the display of information and to reduce distortion. The projection surface may not be flat, such as when an image is projected directly on a patient. In this example, the range data is used to adjust the projected image making the projected image appear as if the image is being projected on a uniformly flat surface.

Three factors that impact the projected image quality and experience are: the image focus (e.g., the image is focused on the desired surface for clarity); the image contrast (e.g., the image provides contrast to show details); and the selectively darkened regions (e.g., regions where the projector does not project light). Image focus (i.e., clarity) can be an issue when employing standard bulb projector technology. It is desirable for the x-ray system to project the sharpest image possible on a given surface. The range data is used to adjust the focus to project a sharper image. For example, the range data may be used to provide a focus-free system, by facilitating the automatic focus of the projected image. In some instances, using laser projection technology can minimize or eliminate focus issues because many laser projection systems do not require focus.

Image contrast and quality can vary depending upon ambient lighting and the projection surface. For example, in most interventional radiology procedures, ambient lighting is low. Low ambient lighting typically provides a suitable environment for projecting images. The projection surface also impacts the quality of the projected image. For example, if the projection surface is a patient or another object, the color of the patient's clothing is selected to provide a better surface for the projected images. In one implementation, an optional radio-transparent surface is placed over a portion of the table 205 or the object being irradiated to provide improved contrast and provide a more uniform surface upon which the images are projected. In this example, the radio-transparent surface is a rigid or semi-rigid cloth. Alternatively, the radio-transparent surface is a lightweight radio-transparent cover placed on the table 205. Other radio-transparent materials are contemplated. The radio-transparent surface is a low-cost accessory that is be used when a higher quality image is desired. Not all of the applications require high quality image to be effective. In another implementation, the output color of image is changed to better interact with the color of the table 205 or the object being irradiated. In this example, the color of the table 205 and/or the object being irradiated and x-ray system is used to adjust the projected image to provide suitable contrast for a quality image. In one example, a color camera detects the color of the table 205 and/or the object being irradiated.

In another example, the range data is used to selectively darken regions of the projected image. In this example, a portion of the projected image is darkened where there is a lack of information or that no information is being displayed. In another example, projecting images on a light-sensitive region of the table or a light-sensitive region of the patient is avoided, such as over the patient's eyes.

In another example, the range data consists of each pixel being labeled by a distance or can also be a series of three-dimensional points in the case of a three-dimensional range scanner. When associated with the projector, the range scanner is a 2D matrix of distances from the x-ray emitter or detector depending upon the implementation. The data is used to automatically orient and configure the table and scanner parameters to the object being irradiated. For example, the range data is used to calibrate the x-ray system during maintenance. In another example, the range scanner is used to automatically configure the x-ray system for a patient for the given procedure. In this example, depending on the given procedure type, range data can automatically adjust the settings (e.g., C-arm position, angular orientation, exposure time, radiation dosage, etc.) for the patient region receiving the procedure. By analyzing the shape of the patient from the range data, the patient's chest or head can be identified to automatically position the table and C-Arms for the intended procedure. Before the procedure, the range scanner data is used to determine the region of the patient that will be imaged and is used to automatically configure the x-ray source for irradiating the region to be imaged. Additionally, the range data is used to track the orientation of the patient and nearby objects in the operating room. The patient orientation can be used to automatically re-configure the C-arm during the procedure. For example, in a heart procedure, the range data is used to identify the patient's torso and the table 205. Using the identified locations, the C-arms are automatically oriented in position for the procedure. The same range data can also be used to identify light-sensitive regions, such as the patient's eyes, and black out the projected image in the light-sensitive regions. Additionally, fluoroscopic images and pre-operative overlay information is projected directly on the region being irradiated. The projected fluoroscopic images and pre-operative overlay information can be dynamically adjusted if the table or C-arms are repositioned.

The range data is also used to prevent collisions within the x-ray system. For example, C-arm movement is limited when obstructions are detected based on the range data. For example, an x-ray system is typically programmed for the location of the table 205 and the other objects that are part of the x-ray system. In this example, the range data is used to prevent the C-arm for colliding with the operator or other staff in the room, with additional equipment used in the procedure, such as surgical trays, or with any other objects that are not preprogrammed in the x-ray system, such as other robotics in the room. In an implementation, the x-ray system would stop all movement when range data values between objects reach a threshold distance (e.g., a value close to zero) or when objects are detected in close proximity to the sensor.

The range data is also used to receive operator inputs. Traditionally, operator inputs are received via operator interface 213. The operator interface 213 includes joysticks and other input devices. Receiving operator inputs from the range data can reduce the operator's reliance on the operator interface 213, and in some instances, eliminate the need for the operator interface 213 altogether. Further, eliminating the operator interface 213 altogether saves preparation time, effort and cost expended sanitizing and prepping (e.g., installing disposable plastic covers) the operator interface 213

For example, the range data is used to augment the operator interface experience allowing the operator to input commands via gestures, such as using hand gestures. The operator's hand creates a range of distance values closer to the scanner and are segmented from the rest of the distance data. The distance values are used to identify individual fingers and are used to identify which gesture the operator is making. In this example, the range scanner dynamically tracks the operator and identifies operator's inputs via gesture recognition functionality. Various gestures are recognized. In an example of gesture recognition, the collimator settings can be adjusted by the operator forming an L-shaped gesture with the operator's hand. The L-shaped gesture signifies a corner of the collimator's aperture, and moving the L-shape gesture adjusts the collimator by increasing or decreasing the size of the aperture. Simultaneously, the projector can project the identified gesture onto the operator's hand as a feedback to make sure the system identified the correct hand gesture and hand location. In another example, overlaid images obtained from pre-operational images are useful for navigation and guidance during a procedure. These overlays are often difficult to enable, disable or adjust with the operator interface 213. Various gestures for moving, aligning, rotating the overlays saves the operator time and effort utilizing the pre-operational images. Another gesture disables or enables the overlays. In yet another example, gestures for frequently used operations allow the operator to have fast and intuitive control of critical functions in the x-ray system without depending on or communicating with support staff for the frequently used functions. In this example, a frequently used function is moving the C-arm. A grabbing and pulling gesture may be used to move the C-arm.

In one implementation, when the range data is also used to receive operator inputs, the region for such inputs can be limited to a set region, such as near the control unit. In another implementation, the projector projects an image on the operator's hand when the x-ray system is receiving an input gesture. For example, a shape, color or other identifier of the gesture is projected on the operator's hand to signify the input gesture. Additionally, a gesture control is used to open additional applications and used to provide direct interfaces to the most often used controls for those additional applications.

Figure 4:
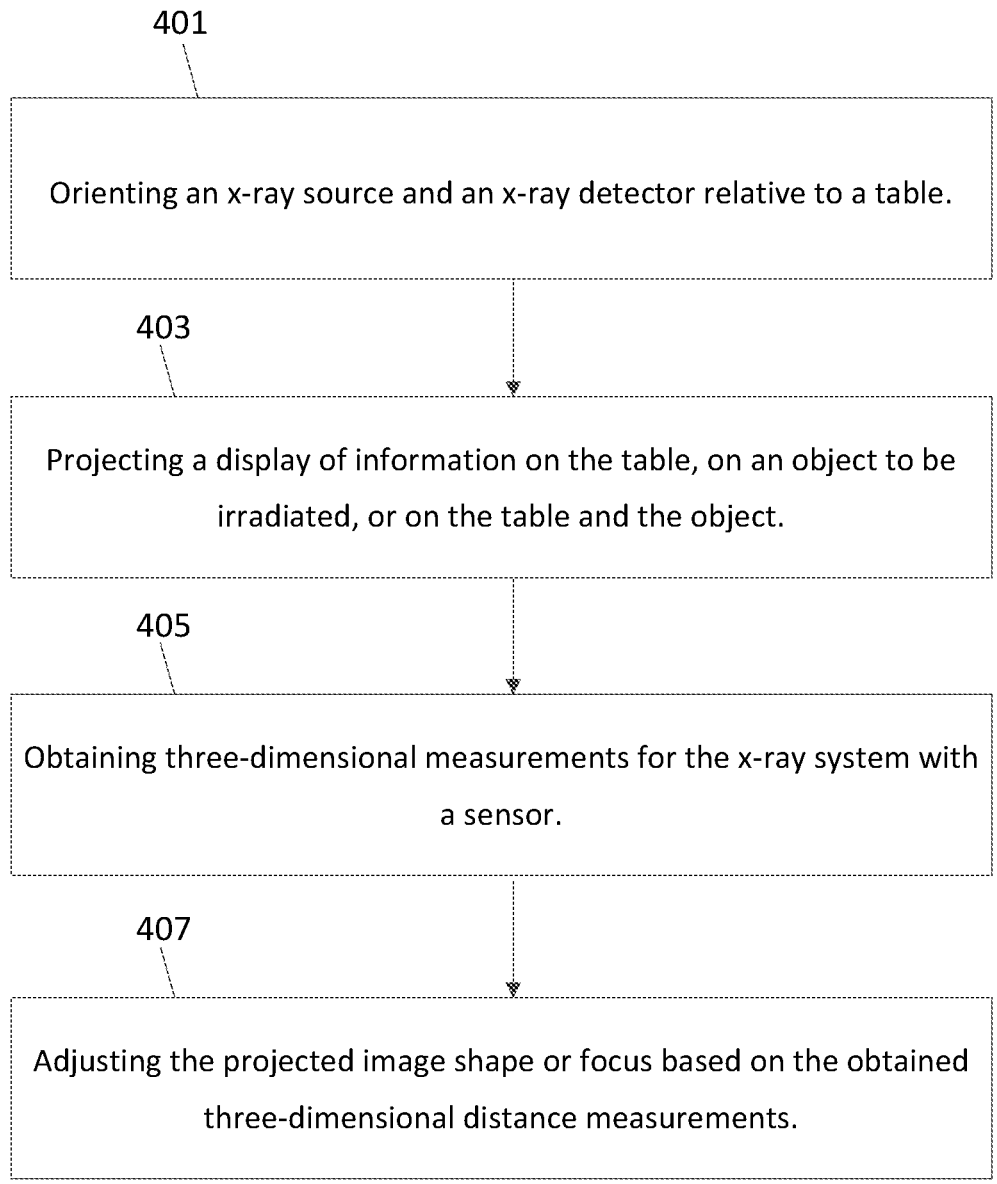
FIG. 4 is a flowchart diagram of an embodiment of a method for a projection display on an x-ray imaging device.

FIG. 4 is a flowchart diagram of an embodiment of a method for a projection display on an x-ray imaging device. The method is implemented by the system of FIGS. 1, 2, 3 and/or a different system. Additional, different or fewer acts may be provided. The method is provided in the order shown. Other orders may be provided and acts may be repeated.

At act 401, an x-ray source and x-ray detector is oriented relative to a table.

At act 403, a display of information is projected on the table, on an object to be irradiated on the table, or on the table and the object. The display of information is projected by one or more projectors. The projected display of information includes an x-ray device state, a patient state, a surgical tool position, an image captured by the x-ray imaging device and/or a marketing image.

At act 405, three-dimensional (3D) distance measurements are obtained for the x-ray system. The three dimensional distance measurements are obtained by a range scanner, a sensor or a range finder. Act 405 may be performed before act 403, so that the projection accounts for the detected ranges or identified parts of the surface onto which the image is projected.

At act 407, the projected image shape or focus is adjusted based on the gathered three-dimensional distance measurements.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

I claim:

1. An x-ray system comprising:
   an x-ray emitter;
   an x-ray detector;
   a table configured to receiving an object to be irradiated;
   an operator interface comprising:
      an projector configured to project a display of information on the table, on the object, or on the table and the object; and
      a sensor configured to capture an image with distance measurements,
      wherein the distance measurements are distances from the sensor.

2. The x-ray system of claim 1, wherein the projected display of information comprises an x-ray system state, a patient state, a surgical tool position, or a marketing image.

3. The x-ray system of claim 1, wherein the projected display of information comprises a fluoroscopy image or a sequence of saved images projected directly on the object.

4. The x-ray system of claim 1, further comprising:
   a radio-transparent surface placed over the object.

5. The x-ray system of claim 4, wherein the radio-transparent surface comprises a cloth.

6. The x-ray system of claim 1, wherein the x-ray emitter or the projector are configurable using the distance measurements.

7. The x-ray system of claim 1, wherein the projector is configured to project the display of information comprising an operator input gesture and location based on the distance measurements.

8. A C-arm x-ray system comprising:
   a C-arm having a first end and a second end;
   an x-ray source mounted to the first end;
   an x-ray detector mounted to the second end;
   a table configured for receiving a patient to be irradiated;
   an operator interface comprising:
      a projector configured to project a display of information on the table, on the patient, or on the table and the patient; and
      a sensor configured to capture an image with distance measurements,
      wherein the distance measurements are distances from the sensor.

9. The C-arm x-ray system of claim 8, wherein the projector is mounted to the C-arm.

10. The C-arm x-ray system of claim 8, wherein the projector is mounted to a fixed location above the table.

11. The C-arm x-ray system of claim 8, wherein the projector is mounted to the C-arm; and further comprising:
    an additional projector mounted to a fixed location above the table.

12. The C-arm x-ray system of claim 11, wherein the projector mounted to the C-arm is configured to project the display of information and the additional projector is configured to project a second display of information.

13. A method for a projection display on an x-ray imaging device, the method comprising:
    orienting an x-ray source and an x-ray detector relative to a table;
    projecting, by a projector, an operator interface including a display of information on the table, on an object to be irradiated on the table, or on the table and the object; and
    obtaining an image with a sensor,
    wherein the image comprises distance measurements that are distances from the sensor, and
    wherein the projected operator interface comprises an x-ray device state of the x-ray imaging device, a patient state, a surgical tool position, an x-ray image captured by the x-ray detector, or a marketing image.

14. The method of claim 13, further comprising:
    adjusting the operator interface based on the distance measurements.

15. The method of claim 14, wherein adjusting the operator interface comprises reducing a distortion by adjusting a projected image shape or a focus of the projected operator interface.

* * * * *